United States Patent [19]

Allison

[11] 3,973,557
[45] Aug. 10, 1976

[54] ELECTRODE

[76] Inventor: Kenneth C. Allison, 1546 S. Shore Drive, Crystal Lake, Ill. 60014

[22] Filed: Apr. 21, 1975

[21] Appl. No.: 569,813

[52] U.S. Cl. .......................... 128/2.06 E; 128/417; 128/DIG. 4
[51] Int. Cl.² ........................................ A61B 5/04
[58] Field of Search ............ 128/2.06 E, 2.1 E, 404, 128/410, 411, 416–418, DIG. 4; 339/244 R

[56] References Cited
UNITED STATES PATENTS

| | | | |
|---|---|---|---|
| 3,623,479 | 11/1971 | Day | 128/2.06 E |
| 3,659,586 | 5/1972 | Johns et al. | 128/2.1 E |
| 3,795,241 | 3/1974 | Golovko | 128/2.06 E |
| 3,828,766 | 8/1974 | Kresnow | 128/2.1 E |
| 3,862,633 | 1/1975 | Allison et al. | 128/2.06 E |

FOREIGN PATENTS OR APPLICATIONS

| | | | |
|---|---|---|---|
| 858,741 | 7/1949 | Germany | 128/417 |
| 6,700,019 | 7/1968 | Netherlands | 128/2.06 E |
| 228,854 | 2/1969 | U.S.S.R. | 128/2.1 R |
| 216,902 | 4/1968 | U.S.S.R. | 128/2.1 E |

*Primary Examiner*—Robert W. Michell
*Assistant Examiner*—Lee S. Cohen
*Attorney, Agent, or Firm*—Anthony S. Zummer

[57] ABSTRACT

A biomedical electrode for use in cooperation with a signal-receiving apparatus is the subject matter of this invention. The electrode includes an open-sided resilient transparent container, with a microporous diaphragm closing the open side. The container includes a filling aperture on the side opposite the open side. The container has three resilient fingers formed integral therewith, which fingers contact the diaphragm to hold the diaphragm outward from the container. The resilient fingers are equiangularly spaced about the filling aperture. An annular sealing flange is formed integral with the container; and extends into the filling aperture. A terminal plug is positioned in the filling aperture, in seaing engagement with the annular sealing flange, to seal closed the filling aperture. The terminal plug includes a cup, which is deformed slightly during insertion of the terminal plug into the filling aperture. The cup has a continuous silver surface on the exterior thereof, extending into the interior of the container. An electrolyte is contained in the container; and permeates the diaphragm to unite with skin fluids of the subject. The electrolyte co-acts with the exterior of the terminal plug to form a silver-silver chloride half cell therewith. The container has a flat open-cell porous annular pad surrounding the container and connected to the container. An open network adhesive is secured to one side of the pad for adhesively securing the electrode to the surface of the subject.

19 Claims, 5 Drawing Figures

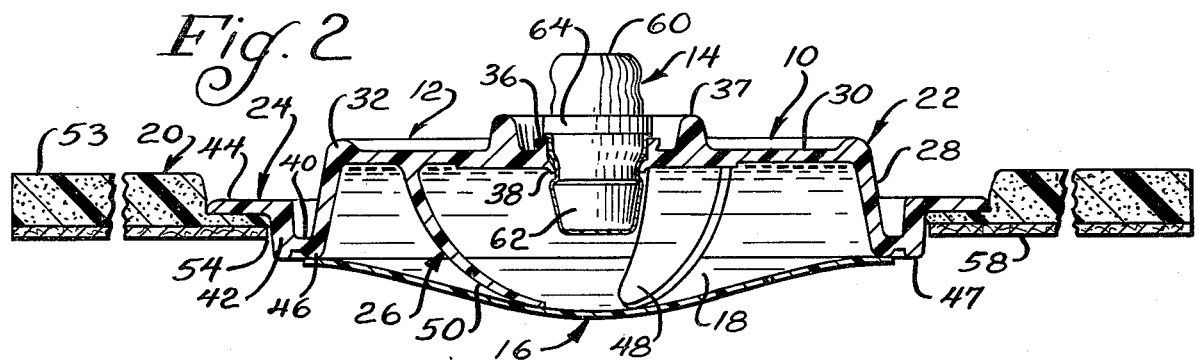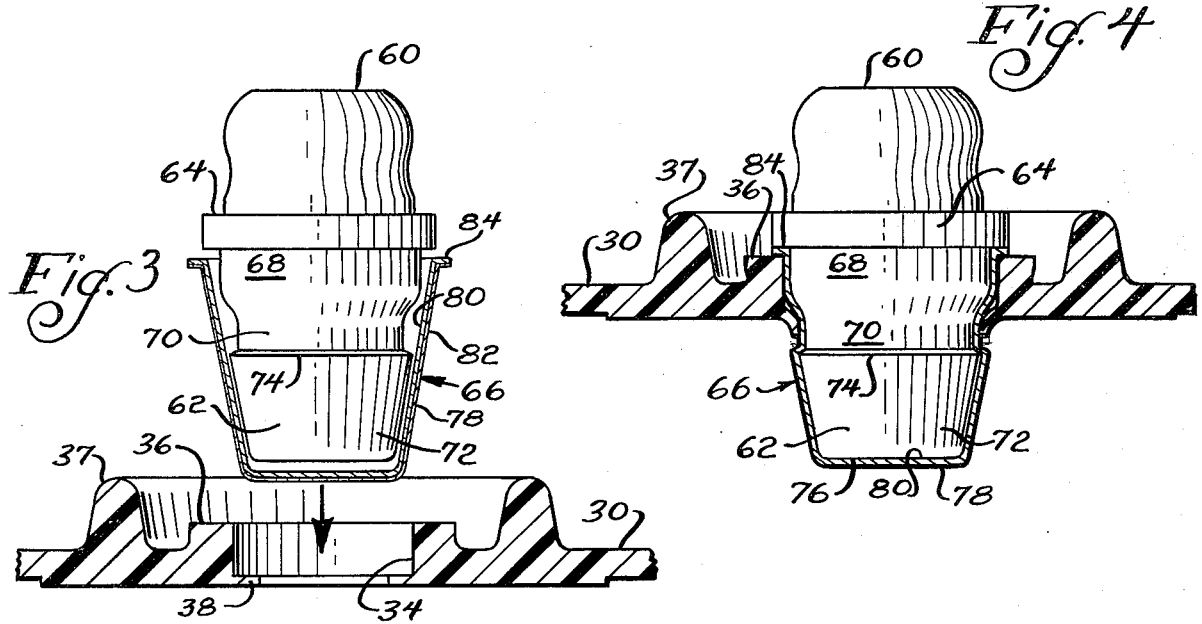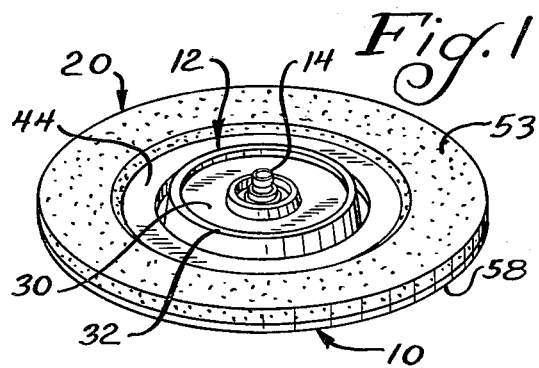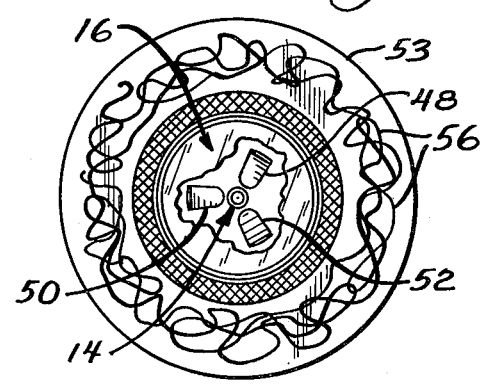

ELECTRODE

BACKGROUND OF THE INVENTION

The general construction of biomedical electrodes of this general type is described in detail in U.S. Pat. No. 3,862,633, issued Jan. 28, 1975, to Kenneth C. Allison and William H. Cooley. The biomedical electrode disclosed in the aforementioned patent is satisfactory for many purposes. In making certain observations, it is particularly desirable to provide a biomedical electrode which utilizes a silver-silver chloride half cell. Silver is expensive; and is to be used sparingly in a disposable biomedical electrode.

Another problem encountered with biomedical electrodes of this general type is that it is often desirable to provide a means for holding the diaphragm outward from the container. During usage, there is a gradual outflow of electrolyte, thereby reducing the volume of electrolyte, which allows the diaphragm to bow inward slightly of the container. Contact between the diaphragm and the surface of the subject may be impaired when the diaphragm bows inward. Furthermore, many practitioners find that they would like to observe the interior of the electrode while applied to a subject, especially after prolonged use.

SUMMARY OF THE INVENTION

The present electrode is a specific improvement of the electrode disclosed in U.S. Pat. No. 3,862,633. The subject electrode has an improved container construction, wherein the container is made of a transparent material; and has three resilient equidistantly-spaced curved fingers formed interiorly of the container. The fingers extend toward the center of the container, and toward each other; and also extend slightly outward. The container also has a filling aperture in its center. The filling aperture is surrounded by the three resilient fingers. A microporous permeable diaphragm is secured to one side of the container to seal closed the container. The diaphragm engages the three resilient fingers, which hold the diaphragm outward from the container. An annular sealing flange is formed integral with the container; and extends into the filling aperture. An open-cell annular mounting pad is secured to the container, with the container in the center of the mounting pad. The mounting pad has an open network adhesive secured to one side to provide a means for adhesively securing the pad to the surface of a subject.

An electrolyte containing chloride is introduced into the container through the filling aperture to fill the container. After the container has been filled, a terminal plug is inserted into the filling aperture into sealing engagement with the container and with the annular sealing flange to seal closed the filling aperture. The terminal plug includes a thin wall cup, having a thin continuous surface of a conductive metal on the outer side, which side extends into the container and into contact with the electrolyte to form a silver-silver chloride half cell with the electrolyte. The balance of the terminal plug is made of a base electrically-conductive material, which is in electrical contact with the exterior of the cup. It is therefore a principal object of this invention to provide an improved biomedical electrode construction which utilizes a continuous metal surface in contact with an electrolyte to form a metal-metal chloride half cell.

It is another object of the present invention to provide an improved construction of a biomedical electrode, in which the diaphragm of the electrode is held outward from the container by a resilient finger which is formed integral with the container.

It is a still further object of the herein-disclosed invention to provide a biomedical electrode which may be quickly and easily manufactured.

Other objects and uses of this invention will become readily apparent to those skilled in the art upon a perusal of the following specification in light of the accompanying drawing.

BRIEF DESCRIPTION OF THE DRAWING

FIG. 1 is a perspective view of a biomedical electrode embodying the present invention;

FIG. 2 is an enlarged cross-sectional view of the electrode shown in FIG. 1, with portions broken away to show better the interior construction thereof;

FIG. 3 is an enlarged side elevational view of a top portion of a container of the electrode of FIG. 1, showing a terminal plug being separated for purposes of illustration, in position for insertion into a filling aperture of the electrode;

FIG. 4 is an enlarged side elevational view similar to FIG. 3, but showing the terminal plug seated in its sealing position in the filling aperture; and FIG. 5 is a bottom view of the biomedical electrode shown in FIG. 1, but with the diaphragm broken away to show better the position of three resilient fingers formed integral with the container, but with a release paper removed, showing an open network adhesive on a pad.

DESCRIPTION OF THE PREFERRED EMBODIMENT

Referring now to the drawing, and especially to FIG. 2, a biomedical electrode which is a specific embodiment of the instant invention is shown therein and is generally indicated by numeral 10. The electrode 10 generally includes a resilient open-sided container 12, a terminal plug 14 sealingly mounted in container 12, a microporous diaphragm 16 sealingly mounted on an open side of container 12, an electrolyte 18 in the container and held therein by diaphragm 16, and an electrode mount 20 secured to the outer periphery of the container 12.

Container 12 is made of a transparent polypropylene, which is resilient and may be conveniently manufactured by injection molding. It is readily apparent that any other suitable transparent material may be used. The container generally consists of three integral parts, namely, a cup 22, a mounting flange 24 formed integral with the cup, and a resilient diaphragm support 26. Cup 22 includes an annular sloping wall 28, with a top 30 formed integral therewith. A ridge ring 32 is formed integral with the outer periphery of top 30 and the upper portion of sloping wall 28. In the center of top 30, there is a filling aperture 34, with a terminal boss 36 formed integral with the top and concentric with the filling aperture 34. A terminal annulus 37 surrounds the boss 36; and is formed integral with top 30. A resilient annular sealing flange 38 is formed integral with the top 30. Flange 38 extends inward into the filling aperture 34 for engagement with terminal plug 14, as is described in detail hereinafter.

Mounting flange 24 includes an annular cup flange 40, formed integral with the lower portion of sloping wall 28. A cylindrical annular wall 42 is formed integral with the outer periphery of flange 40. An annular pad flange 44 has its inner edge formed integral with cylindrical wall 42. An annular diaphragm bead 46 is formed integral with the inner edge of flange 40 for receipt of the diaphragm. An annular sealing ridge 47 is formed integral with flange 40; and is concentric with bead 46.

Resilient diaphragm support 26 includes three identical resilient fingers 48, 50 and 52. Each of the resilient fingers has one end formed integral with top 30. Each of the fingers extends outward of the container; and is curved toward the axis of filling aperture 34. The fingers extend beyond the container to engage diaphragm 16. Each finger has a rounded end; and is tapered to increase the resilience of the finger. The fingers are equiangularly spaced about the filling aperture, so that the terminal plug is surrounded by the resilient fingers.

Electrode mount 20 includes a thin piece of reticulated polyurethane foam pad 53, in which there are 50 to 150 pores per linear inch. Pad 53 has a container aperture 54 in its center; and receives a portion of container 12 therein. An open network adhesive 56 is secured to one side of the polyurethane foam pad. A conventional release paper 58 is positioned over the adhesive to prevent the adhesive from sticking to undesired materials. Pad 53 is secured to the flange 44 by heat sealing.

A well-known conventional sealing sheet (not shown herein) is releasably mounted in sealing engagement with annular sealing ridge 47 of the container to prevent electrolyte from drying out in storage. When the electrode is in use, the sealing sheet is removed so that the diaphragm may contact the surface of a subject.

Terminal plug 14 generally includes a conductive terminal head 60, with a terminal body 62 formed integral therewith and a terminal flange 64 between the head and the body. A terminal cup 66 receives the terminal body 62. The terminal head 60 is adapted for receipt of a conventional terminal connector. The body 62 includes a root portion 68, formed integral with flange 64. Root portion 68 is formed integral with a neck 70, which neck has a tapered nose 72 formed integral therewith. The tapered nose has a shoulder 74 adjacent to the neck 70; and a flat nose end 76 on its free end.

Cup 66 is readily deformable. The cup has a solid silver, or continuous silver, exterior 78. A base 80 of the cup receives the silver exterior 78. The cup includes a body portion 82 and a flange portion 84. The total wall thickness of the cup is 3/1000 of an inch thick. However, any thickness from 2/1000 to 5/1000 of an inch is acceptable. The thickness of the silver exterior is 2/10,000 of an inch. The material of the base 80 of the cup is, in this instance, brass. However, any other suitable material may be used as long as the material is soft and may be readily deformed.

The electrolyte, in this instance, is a physiological saline with 0.9% silver chloride solution, and including a wetting agent, a bacteria inhibitor, and glycerin to limit the evaporation of the electrolyte. The electrolyte is contained in the container by diaphragm 16, which in this instance is a thin sheet of microporous polypropylene, so that the diaphragm is wetted by the electrolyte.

The electrode is assembled by securing diaphragm 16 to the diaphragm bead 46 and securing electrode mount 20 to flange 44. A sealing sheet, which is not shown herein, is placed over the diaphragm; and is releasably sealingly connected to ridge 47 of the container. Cup 22 is filled with electrolyte 18 through filling aperture 34 in a manner such that all of the air is expelled from the container. Once the cup is sufficiently filled, terminal plug 14 is inserted into the filling aperture to seal closed the filling aperture.

The terminal plug is inserted into the filling aperture, with the longitudinal axis of the terminal plug and the filling aperture being aligned. The body of the terminal plug is positioned in the cup. Terminal plug nose 76 is positioned in the bottom of the cup. The terminal plug is then forced down into the filling aperture 34. As the terminal plug moves through the filling aperture, the material of the container is pushed outward, as is sealing flange 38. Since the cup is a thin wall soft material, the container pushes the cup inward against the body 62 to deform the cup into the shape of the body. The terminal plug is pushed down until flange 84 rests on the aperture boss 36. The container, being in tight engagement with the terminal plug, holds the terminal plug in sealing relationship. The sealing flange falls into the neck portion of the deformed cup to hold the terminal plug in position. It may be appreciated that flat nose 76 causes the cup to move downward, rather than be deformed at the bottom portion of the cup, so that all deformation of the cup is radially relative to the body, thereby causing the cup to conform to the body. Once the terminal plug is in position, it may be seen that it is surrounded by the resilient fingers 48, 50 and 52.

The outer surface of the terminal plug is a continuous silver surface. Inasmuch as the diaphragm is permeable to the electrolyte, the outer surface of the diaphragm is wetted by the electrolyte. A light electrical potential is set up across the diaphragm and terminal to start a half cell reaction between the silver of the terminal plug and the silver chloride of the electrolyte.

The electrode is applied to the skin of a subject by removing the release paper 58 from the pad and removing the sealing sheet, which is not shown herein. The electrode is adhesively secured to the subject by positioning the electrode in a desired location and applying a load to pad 53. Diaphragm 16 is secured into contact with the surface of the subject. Inasmuch as diaphragm 16 is microporous, electrolyte 18 permeates the diaphragm to wet slightly the exterior surface of the diaphragm. When the diaphragm is placed into contact with a subject's skin, good contact is made between the diaphragm and the subject's skin fluids without the use of any other material or scraping of the subject's skin. The electrolyte has an opportunity to unite with the natural skin fluids, thereby setting up a direct electrical connection between the lowest layer of the skin and the electrolyte.

Measurements are taken in a conventional fashion, using conventional equipment. The electrical condition is observed on conventional electrical measuring equipment. There is a faithful reproduction of the signal through the electrolyte, united with the skin fluids, to provide a conductive path directly beneath the electrode and a lower layer of the subject's skin through the diaphragm to affect the half cell.

The electrolyte is a physiological saline solution, thus allowing the electrode to remain on a patient's skin for a prolonged period of time. Since a patient may perspire, the open network adhesive on pad 53 allows the perspiration to pass through the adhesive layer and into the open-cell pad 53; and thereby be evaporated without irritating the skin of the patient.

It should further be noted that, in the event that there is any evaporation of the electrolyte from the container, the resilient fingers keep the diaphragm extended outward from the container so that the diaphragm is in good electrical contact with the skin of the patient. The three resilient fingers also form a protective shield around the terminal so that, should a careless operator handle the electrode, the diaphragm would not be punctured on the terminal inasmuch as the resilient fingers would give pursuant to any abnormal pressure on the resilient fingers.

The electrode may be simply and easily discarded by simply pulling the pad off the patient and discarding the entire electrode. The use of a small amount of silver allows the electrode to be manufactured at minimum cost; but still provides an electrode which has a silver-silver chloride half cell, having a high degree of fidelity.

Although a specific embodiment of the present biomedical electrode has been shown and described in detail above, it is readily apparent that those skilled in the art may make various modifications and changes in the specific disclosure contained herein without departing from the spirit and scope of the present invention. It is to be expressly understood that the instant invention is limited only by the appended claims.

What is claimed is:

1. A biomedical electrode for use on a subject for receiving electrical signals from said subject, comprising: a resilient container having an open side, a thin microporous diaphragm sealingly secured to the container closing said open side, a resilient cantilever finger having one end formed integral with the interior of the container, said resilient finger having its free end contacting the interior of the diaphragm to hold the diaphragm outward from the interior of the container, an electrolyte in the container in contact with the diaphragm permeating the diaphragm to wet the outside surface of the diaphragm to have direct contact with a surface of the subject through the diaphragm between said surface of the subject and the electrolyte in the container, said container having a filling aperture, and a terminal plug mounted in said filling aperture in sealing engagement with the container and having a portion in contact with the electrolyte to form a half cell therewith, said terminal plug having a head extending exteriorly of the container adapted for electrical connection to an electrical connector.

2. A biomedical electrode for use on a subject for receiving electrical signals from said subject as defined in claim 1 wherein the terminal plug includes a cup, said cup having a portion positioned in the interior of the container in contact with the electrolyte, said cup portion having a continuous conductive metal outer surface in contact with the electrolyte.

3. A biomedical electrode for use on a subject for receiving electrical signals from said subject as defined in claim 2 wherein the cup is readily deformable and is partially formed upon insertion of the terminal plug into the filling aperture.

4. A biomedical electrode for use on a subject for receiving electrical signals from said subject as defined in claim 2 wherein the terminal plug includes a body formed integral with the head, the body has a flat portion on the end opposite the head, said cup has a flat portion receiving the flat portion of the body.

5. A biomedical electrode for use on a subject for receiving electrical signals from said subject as defined in claim 1, including at least two additional resilient cantilever fingers formed integral with the interior of the container, said additional resilient fingers being identical in construction to the first-mentioned resilient finger and being in contact with the diaphragm, said resilient fingers being equiangularly positioned about the filling aperture, said filling aperture being equidistant from each of the resilient fingers.

6. A biomedical electrode for use on a subject for receiving electrical signals from said subject as defined in claim 5 wherein the resilient fingers are curved and extend inwardly toward each other.

7. A biomedical electrode for use on a subject for receiving electrical signals from said subject as defined in claim 1 wherein the resilient container is transparent.

8. A biomedical electrode for use on a subject for receiving electrical signals from said subject as defined in claim 1, including an annular open-cell foam pad connected to and surrounding the container, and an open network of adhesive on one surface of the foam pad, said open network of adhesive being on the same said as the diaphragm for adhesively securing the pad and the container to the surface of the subject.

9. A biomedical electrode for use on a subject for receiving electrical signals from said subject as defined in claim 1 wherein the terminal plug includes a cup, said cup having a portion positioned in the interior of the container in contact with the electrolyte, said cup portion having a continuous silver outer surface in contact with the electrolyte to form the half cell therewith, and the resilient container being transparent.

10. A biomedical electrode for use on a subject for receiving electrical signals from said subject as defined in claim 1 wherein the resilient container is transparent, and including at least two additional resilient cantilever fingers formed integral with the interior of the container and contacting the interior of the diaphragm, said additional resilient fingers being identical in construction to the first-mentioned resilient finger, said resilient fingers being equiangularly positioned about the filling aperture, said filling aperture being equidistant from each of the resilient fingers, said resilient fingers being curved and extending inward toward each other.

11. A biomedical electrode for use on a subject for receiving electrical signals from said subject as defined in claim 1 wherein the resilient container is transparent, and including an annular open-cell foam pad connected to and surrounding the container, and an open network of adhesive on one surface of the foam pad, said open network of adhesive being on the side of the pad adjacent to the diaphragm for adhesively securing the pad and the container to the surface of the subject.

12. A biomedical electrode for use on a subject for receiving electrical signals from said subject as defined in claim 1 wherein the terminal plug includes a cup, said cup having a portion positioned in the interior of the container in contact with the electrolyte, said cup portion having a continuous silver outer surface on that portion positioned in the interior of the container in contact with the electrolyte, and including an open-cell foam pad connected to and surrounding the container, and an open network of adhesive on one surface of the pad, said open network of adhesive being adjacent to the diaphragm for adhesively securing the pad and the container to the surface of the subject.

13. A biomedical electrode for use on a subject for receiving electrical signals from said subject as defined in claim 1 wherein the terminal plug includes a cup, said cup having a portion positioned in the interior of the container in contact with the electrolyte, said cup portion having a continuous silver outer surface in contact with the electrolyte to form a half cell therewith, and including at least two additional resilient cantilever fingers formed integral with the interior of the container and holding the diaphragm outward, said additional resilient fingers being identical in construction to the first-mentioned resilient finger, said resilient fingers being equiangularly positioned about the filling aperture, said filling aperture being equidistant from each of the resilient fingers.

14. A biomedical electrode for use on a subject for receiving electrical signals from said subject as defined in claim 1 wherein the terminal plug includes a body formed integral with the head, the body has a flat portion on the end opposite the head, a cup mateably receiving the body and having a flat portion mating with the flat portion of the body, said cup having a portion positioned in the interior of the container in contact with the electrolyte, and said cup portion having a continuous silver outer surface on that portion positioned in the interior of the container in contact with the electrolyte to form a half cell with the electrolyte, said cup being readily deformable and being partially formed upon insertion of the terminal plug into the filling aperture and sealingly engaging the container.

15. A biomedical electrode for use on a subject for receiving electrical signals from said subject as defined in claim 1, including at least two additional resilient cantilever fingers formed integral with the interior of the container contacting the diaphragm, said additional resilient fingers being identical in construction to the first-mentioned resilient finger, said resilient fingers being equiangularly positioned about the filling aperture, said filling aperture being equidistant from each of the resilient fingers, each of said resilient fingers being curved and extending toward the other two fingers, an annular open-cell foam pad connected to the exterior of and surrounding the container, and an open network of adhesive on a surface of the pad being in substantially the same plane as the diaphragm for adhesively securing the pad and the container to the surface of the subject.

16. A biomedical electrode for use on a subject for receiving electrical signals from said subject as defined in claim 1 wherein the resilient container is transparent, and including at least two additional resilient cantilever fingers formed integral with the interior of the container and contacting the interior of the diaphragm, said additional resilient fingers being identical in construction to the first-mentioned resilient cantilever finger, said resilient cantilever fingers being equiangularly positioned about the filling aperture, said filling aperture being equidistant from each of the resilient fingers, an annular open-cell foam pad connected to and surrounding the container, and an open network of adhesive on one surface of the foam pad, said open network of adhesive being in substantially the same plane as the diaphragm for adhesively securing the pad and the container to the surface of the subject with the diaphragm in contact with the surface of the subject.

17. A biomedical electrode for use on a subject for receiving electrical signals from said subject as defined in claim 1 wherein the terminal plug includes a body formed integral with the head, a cup mateably receiving the body, said cup having a portion positioned in the interior of the container in contact with the electrolyte, said cup portion having a continuous silver outer surface on that portion positioned in the interior of the container in contact with the electrolyte to form a half cell therewith, said cup being readily deformable and being partially formed upon insertion of the terminal plug into the filling aperture, said resilient container being transparent, and including two additional resilient cantilever fingers formed integral with the interior of the container and engaging the diaphragm, said two additional resilient fingers being identical in construction to the first-mentioned resilient finger, said three resilient fingers being curved and extending toward each other, said resilient fingers being equiangularly positioned about the filling aperture, said filling aperture being equidistant from each of the resilient fingers, an annular open-cell foam pad connected to and surrounding the container, and an open network of adhesive on one surface of the foam pad, said open network of adhesive being on the same side of the electrode as the diaphragm for adhesively securing the pad and the container to the surface of the subject and holding the diaphragm in contact with the surface of the subject.

18. A biomedical electrode for use on a subject for receiving electrical signals from said subject, comprising: a resilient container having an open side, a thin microporous diaphragm sealingly secured to the container closing said open side, an electrolyte in the container in contact with the diaphragm permeating the diaphragm to wet the outside surface of the diaphragm to have direct contact with a surface of the subject through the diaphragm between said surface of the subject and the electrolyte in the container, said container having a filling aperture, and a terminal plug mounted in said filling aperture, said terminal plug including a head extending exteriorly of the container adapted for electrical connection to an electrical connector a body formed integral with said head, and a cup mateably receiving said body, said cup having a continuous silver outer surface in contact with the electrolyte to form a half cell therewith, said cup being positioned in the filling aperture to seal closed the filling aperture.

19. A biomedical electrode for use on a subject for receiving electrical signals from said subject as defined in claim 18 wherein the container is transparent, and including a resilient diaphragm support mounted in the container holding the diaphragm outward from the container.

* * * * *

UNITED STATES PATENT OFFICE
CERTIFICATE OF CORRECTION

PATENT NO. : 3,973,557
DATED : August 10, 1976
INVENTOR(S) : Kenneth C. Allison

It is certified that error appears in the above-identified patent and that said Letters Patent are hereby corrected as shown below:

In the Abstract, Line 14, "seaing" should be --sealing--.

In Claim 8, Line 7, "said" should be --side--.

In Claim 18, Line 15, after "nector", insert --,--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*